(12) United States Patent
Droznin et al.

(10) Patent No.: US 6,793,620 B1
(45) Date of Patent: Sep. 21, 2004

(54) MALE SEXUAL AID

(76) Inventors: Vadim Droznin, 312 Brook St., Carlisle, MA (US) 01741; Henry Droznin, 218 North Rd., Bedford, MA (US) 01730

( * ) Notice: Subject to any disclaimer, the term of this patent is extended or adjusted under 35 U.S.C. 154(b) by 0 days.

(21) Appl. No.: 10/780,953

(22) Filed: Feb. 19, 2004

(51) Int. Cl.$^7$ .................................................. A61F 5/00
(52) U.S. Cl. ........................................ 600/39; 600/41
(58) Field of Search ............ 600/38–41; 604/347–353; 128/842–845

(56) References Cited

U.S. PATENT DOCUMENTS

| | | | | |
|---|---|---|---|---|
| 2,899,957 A | * | 8/1959 | Briggs | 600/39 |
| 4,872,447 A | * | 10/1989 | Tsirjulnikov et al. | 600/39 |
| 4,893,616 A | * | 1/1990 | Immonen | 600/39 |
| 5,928,134 A | * | 7/1999 | Vergara | 600/38 |

* cited by examiner

*Primary Examiner*—John P. Lacyk

(57) ABSTRACT

A prosthesis for male sexual aid comprises a semi-rigid sleeve of thermoplastic material and two straps of elastomeric material. The sleeve has a cutout along its whole length and shaped outside in three portions: a head, a shaft, and a base. A base portion is slanted about the cutout toward the shaft portion. The first strap is secured by both ends to the base portion of the sleeve in a location that is opposite to the cutout. The second strap is an O-ring and secured to the shaft portion of the sleeve embracing the last. In usage, a penis is inserted into the sleeve, the first strap is pulled under the scrotum, the second strap holds the penis inside the sleeve. The first strap being under a fulcrum of rotation of the prosthesis will pull it into a "flaccid" position doing it invisible to an observer when a user is dressed. A moment before a sexual intercourse the user give lift to the prosthesis by his hand. Now, the first strap is above the fulcrum and pulls the prosthesis into the "erected" position. Thus, the user can be comfortably prepared way before a foreseen sexual intercourse. The easy switch from one position to another is achieved by the right interconnection between a slant angle of the base portion of the sleeve and the location of the point where the first strap is secured to the sleeve.

5 Claims, 3 Drawing Sheets

MALE SEXUAL AID

CROSS REFERENCE TO RELATED APPLICATIONS

Not applicable

STATEMENT REGARDING FEDERALLY SPONSORED RESEARCH OR DEVELOPMENT

Not applicable

REFERENCE TO A MICROFISH APPENDIX

Not applicable

BACKGROUND OF THE INVENTION

The present invention relates generally to the prosthesis devices for lifting a flaccid penis into a supporting position in a way to accommodate sexual intercourse. In particular, the prosthesis according to the present invention is a purely mechanical structure and does not interfere with blood flow to the penis. It may be used by males suffering from impotency due to actually any medical or psychological reasons.

Male sexual aid devices are known. Some of them include a cover which is put on the penis and connected with a source of vacuum (see, for example, U.S. Pat. No. 4,671, 262). Such devices are however bulky, since they are connected with a vacuum pump. As a result, the user experiences a discomfort, which affects the physiological process of sexual intercourse.

Devices of purely mechanical prosthesis type where no air flow is used are also known (see, for example, U.S. Pat. No. 5,666,971). Those device has a ring-shape base with two walls spaced from one another to define a cavity in between, a cylindrical elastic closed cover connected to the base and having a portion which is arcade-shaped and adapted to cover the head of the penis. The devise also has relatively long middle portion which is adapted to cover the shank of the penis. In use, a closed elastic strap is pulled from the lower base portion and under the scrotum, and another strap is pulled from the upper base portion and around the torso of the user. By those, the prosthesis assumes a position that is approximately in perpendicular relationship to the torso. As a matter of course, all those preparations have to be done just before the sexual intercourse, that is very awkward and inconvenient.

What needed is a prosthesis device of a simple structure, not bulky and purely mechanical type that can be prepared by the user for some period of time before a foreseen sexual intercourse. The device needs to be reliably secured in the "flaccid" (invisible) position for any needed period of time, and then to be switched into the reliably secured "erected" position in no time and with ease.

BRIEF SUMMARY OF THE INVENTION

In accordance with the present invention the sexual aid device is an elongated sleeve with a cutout along its whole length. There are three basic portions are formed on the sleeve: a base, a shaft and a head. The base portion and the head portion are thicker than the shaft. Two elastic straps are also provided. The first elastic strap has two ends which are secured to the base portion forming a ring. The second elastic strap constitutes an O-ring that is secured to the outside surface of the shaft and embraced it.

The inside diameter of the sleeve corresponds the diameter of the penis. Same is the length of the sleeve. The sleeve is made of a semi-rigid material, for example a thermoplastic, that is comfortable enough to contact the genitals. Being rolled in a sleeve, even not in closed one, the material provides a resistive condition to the bending load. At the same time, walls of the cutout in the sleeve can be easily moved apart with lateral loads from inside out. The head portion of the sleeve is shaped to be alike the penis glans with the corona sulcus. The shaft (the thinnest portion of the prosthesis) is shaped alike the penis shank. The base portion is shaped thicker than the shaft to receive and reliably secure the ends of the first strap and for providing more comfortable contact with torso and genitals. The base portion is slanted toward the shaft portion. It is turned to an angle about the point located at the end of the cutout of the sleeve. Location of the ends of the first strap is interconnected with the angle of the slant. The turning point of the base portion should be located in between the two positions of the first strap: one position when the strap is parallel to the longitudinal axis of the sleeve, and another position when the strap is perpendicular to the same axis. This interconnection is true if the strap is rotated toward the cutout of the sleeve.

For the use, the penis is embraced by the sleeve of the prosthesis, the first elastic strap is pulled under the scrotum, and the second elastic strap is embraced the shank of the penis. Because of the flexibility of the sleeve along its longitudinal axis, the sleeve comfortably snug the penis. The prosthesis may provide two conditions: the flaccid and the erected. If the first elastic strap is situated under the base of the penis (or, in other words, under the fulcrum of rotation), the force of tension of the strap holds the prosthesis downward. If it is above the fulcrum, the strap holds the prosthesis upward. In order to switch the prosthesis from one position to another, the user just turns it by hand either up or down.

Thus, a simple, comfortable and convenient in usage device is provided. It is reliably holding the prosthesis in two positions: flaccid and erected, with possibility of easy and fast switch from one position to another. Those two positions are the closest to the conditions of a healthy man.

It is an object of the present invention to have a device that can be conveniently prepared beforehand a foreseen sexual activity. Being prepared the device shall be invisible for an observer when a bearer is dressed.

It is another object of the present invention to have a device that is easily switched from one position to another. Switch shall not be connected to any complicated readjustment of a preliminary prepared device. Switch shall be done in a way as it is natural.

It is a further object of the present invention to have a device wherein the easy and fast switch function is provided only by a proper location of the ends of an elastic element on the prosthesis in proportion to the device base configuration.

It is an advantage of the present invention to have a sexual aid prosthesis that can be totally prepared way beforehand, is invisible for an observer in a flaccid position, and can be switched momentarily into an erected position by the user with simple and fast turn.

DETAILED DESCRIPTION OF THE INVENTION

Figure 1:
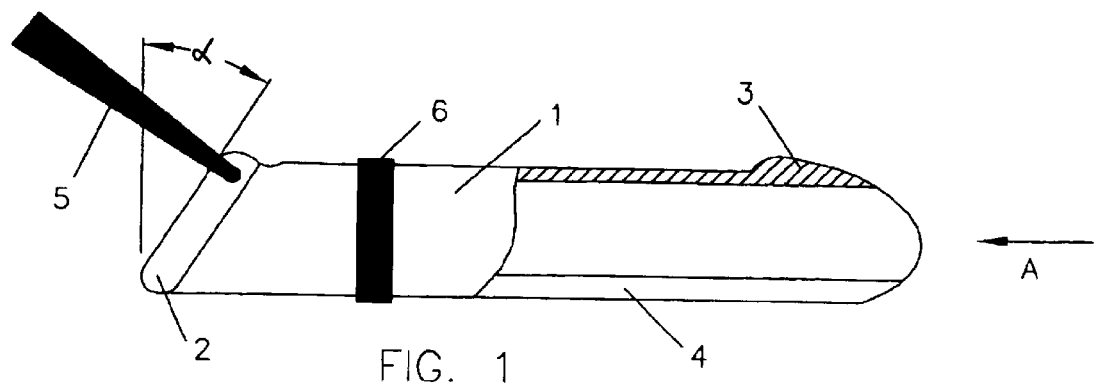
FIG. 1 is a side view of the device according to the present invention with a partial section along a longitudinal axis.
Figure 2:
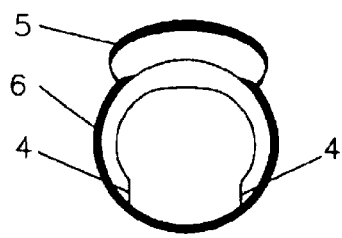
FIG. 2 is a view of the device along arrow "A" to FIG. 1.

Referring to FIG. 1 and FIG. 2 the structure according to the present invention includes a sleeve 1 having a base portion 2 and a head portion 3. The sleeve 1 has a cutout along its whole length that constitutes two walls 4. At the base portion 2 of the sleeve 1 a first elastic strap 5 is secured by its both ends to a location that is opposite to the cutout. A second elastic strap 6 is situated on the sleeve 1 and embraces it. The strap 6 is an O-ring.

The sleeve 1 having actually three portions: the base portion 2, the head portion 3 and a portion that is situated between portions 2 and 3 which may be called a shaft portion. This is the longest and thinnest portion of the sleeve 1. On the head portion 3 a swelling is formed outside the sleeve 1 that is shaped as glans and corona sulcus of a human penis. The base portion also increased in thickness having outside bead to reliably secure the first elastic strap 5 and avoid sharp edges. Both straps 5 and 6 are made of elastomeric material. The sleeve 1 is made of thermoplastic or similar semi-rigid material that is comfortable for contact with a human body.

Thickness of the sleeve 1 provides easiness for moving walls 4 apart, but adequate rigidity to resist to bending loads which can be applied to the sleeve 1. Resistance to bending is provided because of almost circular cross section of the sleeve 1. Resistance to moving apart the walls 4 is provided by mostly rectangular cross section of thin material of the sleeve 1. It is easy to see that the last resistance is much lower than the first one, because diameter of the sleeve 1 is substantially larger that its walls thickness.

Base portion 2 is slanted toward the shaft of the sleeve 1 at angle $\alpha$ (see FIG. 1). To provide the slant the portion 2 is turned to angle $\alpha$ about a point that is located between walls 4 in the middle of the portion 2. Location of a place where the strap 5 is secured to the portion 2 of the sleeve 1 and the angle $\alpha$ are interconnected. If the strap 5 is rotated (counter clockwise to FIG. 1) from a position that is parallel to longitudinal axis of the sleeve 1 into a position that is perpendicular to the same axis, the turning point of the slant of portion 2 shall be located between those two positions of the strip 5.

Figure 3:
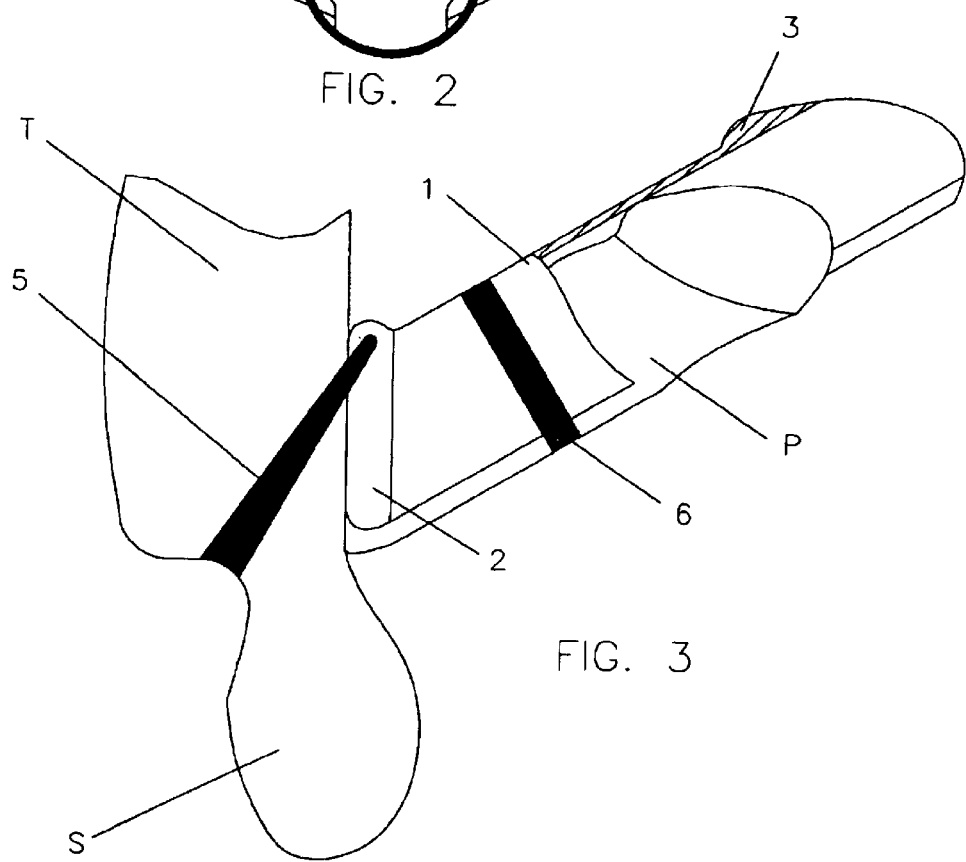
FIG. 3 is a side view of the partially sectioned device in use in the erected position.
Figure 4:
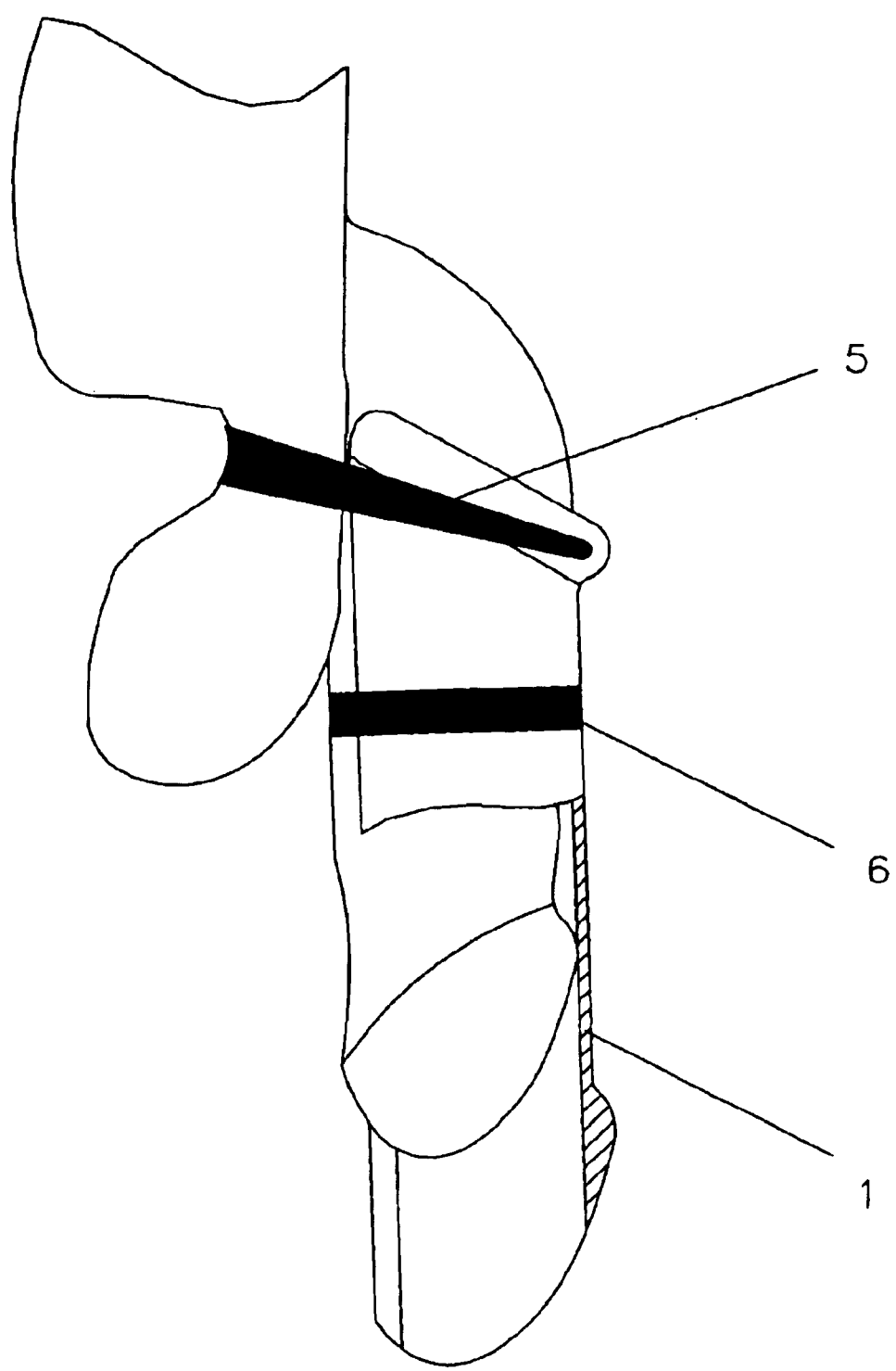
FIG. 4 is a side view of the partially sectioned device in use in the flaccid position.

Referring to FIG. 3 and FIG. 4 the device according to the present invention is shown in usage. In preparation, a user inserts penis P into the sleeve 1 till the base portion 2 is making contact to a user's torso T. The strap 6 is embracing both the sleeve 1 and the penis P. The strap 5 is pulled under the scrotum S. In the position of the device shown in FIG. 3, the prosthesis is ready to accommodate sexual intercourse. In this position the strap 5 lifts and reliably holds the prosthesis in the supporting condition because the strap 5 is situated above the turning point. Being above the turning point the strap 5 tend to rotate the prosthesis all the way until the full contact of slanted base portion 2 and torso T is made. The strap 6 is holding the penis P within the sleeve 1. The prosthesis can accommodate an enlargement of the penis P both in length (it is longer then the penis) and in diameter (the walls 4 of the cutout can easily be moved apart). Sensibility is also provided to a user during the sexual intercourse because a large portion of the penis is exposed through the cutout in the sleeve 1.

If any period of time needed between preparation of the prosthesis and its usage, the user just turns the prosthesis down into a position shown on FIG. 4. When turning, the strap 5 moved into position where the turning point is situated above the strap 5. In this position the strap 5 tends to rotate the prosthesis all the way until the full contact of the penis P and scrotum S is made. In this position the prosthesis is actually invisible for an observer (same as a flaccid penis). Thus, the user can totally prepare the prosthesis way beforehand. Now, it is enough to turn the device counter clockwise to FIG. 4 till the turning point will be under the strap 5, and the prosthesis is ready to accommodate sexual intercourse. It may be done just a moment before the intercourse begins.

Figure 5:
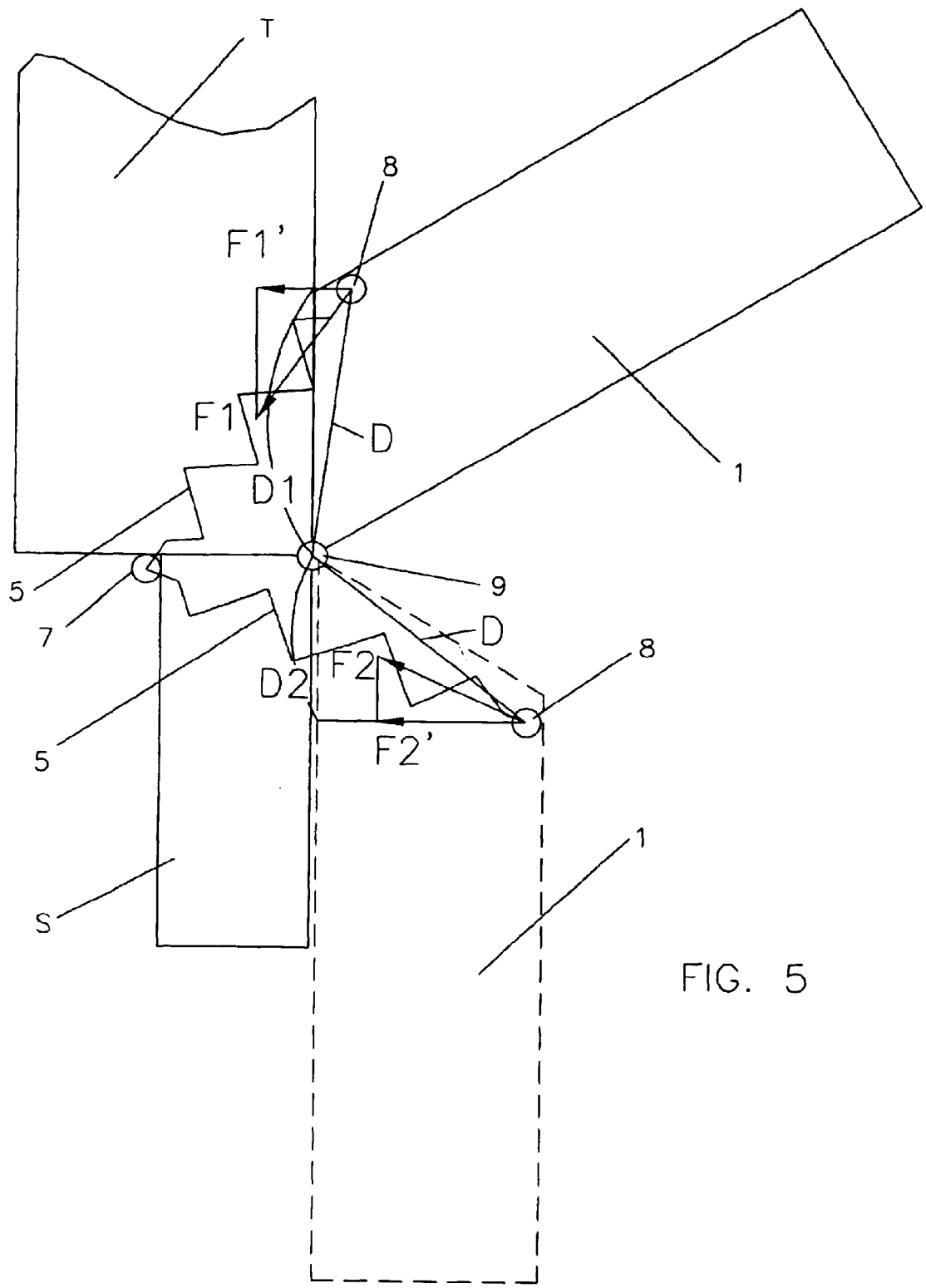
FIG. 5 is a mechanical representation of the device in use showing how it works.

In the mechanical representation of the device showing how it works (see FIG. 5) the point under the scrotum S where the strap 5 (shown as a tension spring 5) is pulled, is designated by number 7. The point where the strap 5 (tension spring 5) is secured to the sleeve 1 (shown as a trapezoidal bar 1) is designated by number 8. The turning point (the fulcrum) is designated by number 9. The sleeve 1 in the erected position in this representation is shown in continuous lines, in flaccid position it is shown in dotted lines. It is easy to see that point 8 in the erected position is situated above the point 9, and under the point 9 in the flaccid position. Distance D between points 8 and 9 in both position is the same, but between points 7 and 8 may be different (D1 and D2). Force of the strap 5 tension may also be different (F1 and F2) depending on the strap elongation in the two shown positions. Thus, the torque that tends to rotate the sleeve 1 into each of the positions may also be different (F1'×D1 and F2'×D2). Locations of the turning point, the point of securing the ends of the strap 5 to the sleeve 1, and also angle $\alpha$ are interconnected. This representation shows that by simply changing location of point 8 or angle $\alpha$ (shown in FIG. 1) the torque in both position may be adjusted to what is needed. This adjustment may be done during a design stage, using simple calculations (as shown above) of the appropriate torque in both positions of the prosthesis. Several options with different torque can be proposed to market. But one condition shall be always abide by designers: the strap 5 shall always intersect the turning point 9 when the prosthesis is turned from one position to another.

So, simple in structure and usage device is proposed as male sexual aid which provides the closest features to natural conditions. While the invention having been described in detail, it is clear that there are variations and modifications to this disclosure here and above which will be readily apparent to one with ordinary skill in the art. For example, material and shape of the sleeve and straps may vary. To the extend that such variations and modifications provide the condition of crossing the turning point 9 by the strap 5 when the last is turned as described above, such are deemed within the scope of the present invention.

We claim:

1. A male sexual aid device, comprising:

a sleeve having a head, a shaft and a base portions;

a first strap having two ends;

a second strap shaped as a closed ring, wherein said sleeve having a cutout along its whole length, said first strap is secured by said two ends to said base portion of said sleeve in a location opposite to said cutout, said second strap is secured to said shaft portion outside said sleeve and embraces said shaft portion, said base portion is slanted to an angle toward said shaft portion about an axis located in said cutout in a middle of said base portion, and said location of said two ends of said first strap is interconnected with said angle in a way that being rotated 90 degrees from a position alongside and out said sleeve toward said cutout said first strap intersects said axis of said slant.

2. A device as recited in claim 1, wherein said head portion is shaped alike a glans with a corona sulcus of a penis, said base portion is shape as a narrow bead, said two ends of said first strap are secured in a middle of said bead, and said shaft portion is the longest and thinnest portion of said device.

3. A device as recited in claim 1, wherein said sleeve is made of thermoplastic.

4. A device as recited in claim 1, wherein said first and second strap are made of elastomeric material.

5. A device as recited in claim 1, wherein a thickness of said sleeve is such that some flexibility is provided for forces applied inside out of said sleeve to widen said cutout, and rigidity is provided for forces applied to bend said sleeve alongside.

* * * * *